United States Patent [19]
Wild et al.

[11] Patent Number: 5,545,736
[45] Date of Patent: Aug. 13, 1996

[54] 6-THIONO-5,6-DIHYDRO-DIBENZ[B,E] AZEPIN-11-ONE-11-OXIMES

[75] Inventors: Hanno Wild, Wuppertal; Wolfgang Roeben, Bergisch Gladbach; Arnold Paessens, Haan; Jörg Petersen-von Gehr, Bochum, all of Germany

[73] Assignee: Bayer Aktiengesellschaft, Leverkusen, Germany

[*] Notice: The term of this patent shall not extend beyond the expiration date of Pat. No. 5,416,209.

[21] Appl. No.: 370,000

[22] Filed: Jan. 9, 1995

Related U.S. Application Data

[63] Continuation of Ser. No. 978,553, Nov. 19, 1992, abandoned.

[30] Foreign Application Priority Data

Nov. 27, 1991 [DE] Germany ............... 41 38 908.5

[51] Int. Cl.$^6$ ............... C07D 223/20; A61F 31/55
[52] U.S. Cl. ............... 540/522
[58] Field of Search ............... 540/522

[56] References Cited

U.S. PATENT DOCUMENTS

| | | | |
|---|---|---|---|
| 3,431,257 | 3/1969 | Aichinger et al. | 260/239.3 |
| 5,385,899 | 1/1995 | Wild et al. | 540/522 |
| 5,416,209 | 5/1995 | Wild et al. | 540/522 |

FOREIGN PATENT DOCUMENTS

| | | |
|---|---|---|
| 0419861 | 4/1991 | European Pat. Off. . |
| 0429987 | 6/1991 | European Pat. Off. . |

OTHER PUBLICATIONS

Burge, Medicinal Chemistry p. 75(1970) Wiley Intescord.
The Chemistry of Organic Compounds, p. 333(1939) the MacMillan Co.
Methods in Enzymology, vol. XXXIV, "Affinity Techniques, Enzyme Purification: Part B", Bovine Trypsin and Thrombin, Hixson, Jr. and A. H. Nishikawa, pp. 440–448, Academic Press, 1974.
Methods in Enzymology, vol. XXXIV, "Affinity Techniques, Enzyme Purification: Part B", Chymotrypsin(s), Tomlinson, et al., pp. 415–420, Academic Press 1974.
Affinity Chromatography, Biospecific Sorption; "Affinity Chromatography of Chymotrypsin on Soybean Trypsin Inhibitor Sepharose: Applications In Genetics And Nuclide Labelling", Gabel, Kasche, Amneus and Lundqvist, pp. 99–102, Pergamon Press, 1977.

Applied Microbiology and Biotechnology, Springer–Verlag 1979, Biotechnol. 6.; p. 195 (1979); "Recovery of Free Enzymes from Product Liquors by Bio–Affinity Adsorption: Trypsin Binding by Immobilised Soybean Inhibitor", Halling and Dunnill.

The Journal of Biological Chemistry, vol. 255, No. 15, Aug. 10, 1980, p. 7089, "Human Red Cell Purine Nucleoside Phosphorylase, Purification By Biospecific Affinity Chromatography and Physical Properties", Osborne, Mar. 17, 1980.

Hoppe–Seyler's Z. Physiol. Chem., vol. 361, p. 543, Apr. 1980, "Purification of Human and Bovine Alkaline Phosphatases by Affinity Chromatograph", Mossner, Boll and Pfleiderer.

Analytical Biochemhistry, vol. 107, p. 341, (1980), "Affinity Chromatographic Sorting of Carboxypeptidase A and its Chemically Modified Derivatives", Cueni, Bazzone, Riordan & Vallee, Mar. 31, 1980.

Hoppe–Seyler's Z. Physiol. Chem., vol. 359, p. 1019, Aug. 1978, "Affinity Chromatograph of Bovine Bran β–Hexosaminidases with Substrate As Affinity ligand"., Lisman and Overdijk, May 1978.

Biochem. J. (1978), vol. 175, p. 125, "Purification of the Hexokinases by Affinity Chromatography on Sepharose––N–Aminoacylglucosamine Derivatives", Wright, Warsy, Holroyde and Trayer, Feb. 1978.

Archives of Biochemistry and Biophysics, vol. 198, No. 2, Dec., 1979, p. 533, "Quantitive Affinity Chromatograph of α–Chymotrypsin", Dunn and Gilbert, Aug. 10, 1979.

Understanding Enzymes, Third Ed. (Horwood Press, 1991), pp. 309–310, Trevor Palmer.

Potent and Selective Inhibition of HIV–1 Replication Invitro by a Novel Series of Tibo Derivatives, vol. 343, Nature, Feb. 1, 1990, pp. 470–473, Rudi Pauwels, et al.

J. Med. Chem. 34, 2922 (1991).

J. Med. Cehm. 34, 2231, (1991).

Biochemistry 30, 2022 (1991).

E. L. Eliel, Stereochemistry of Carbon Compounds, McGraw Hill, 1962 Journal of Virological Methods 20, (1988), 309–321.

*Primary Examiner*—Nicholas Rizzo
*Attorney, Agent, or Firm*—Sprung Horn Kramer & Woods

[57] ABSTRACT

The invention relates to 6-thiono-dibenz[b,e]azepines, to a process for their preparation and to their use as inhibitors of reverse transcriptase and in particular as antiretroviral agents.

3 Claims, No Drawings

6-THIONO-5,6-DIHYDRO-DIBENZ[B,E] AZEPIN-11-ONE-11-OXIMES

This application is a continuation of application Ser. No. 07/978,553, filed on Nov. 19, 1992, now abandoned.

The invention relates to 6-thiono-dibenz[b,e]azepines and to a process for their preparation.

It is already known that substituted 5,6-dihydro-dibenz [b,e]azepin-6,11-dione-11-oximes have a psychotropic action.

The present invention relates to 6-thionodibenz[b,e] azepines of the general formula (I)

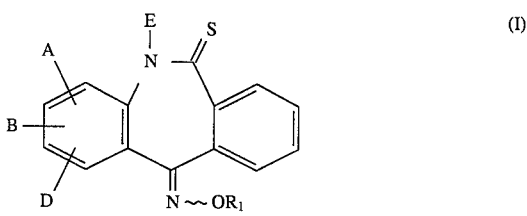

in which

A, B and D are identical or different and represent hydrogen, amino, nitro, halogen, cyano, hydroxyl, trifluoromethyl, trifluoromethoxy or straight-chain or branched alkyl or alkoxy each having up to 8 carbon atoms, E represents hydrogen or straight-chain or branched alkyl having up to 6 carbon atoms, $R^1$ represents hydrogen or represents cycloalkyl having 3 to 6 carbon atoms or represents 2-tetrahydropyranyl, represents straight-chain or branched acyl having up to 8 carbon atoms, or represents straight-chain or branched alkyl or alkenyl each having up to 10 carbon atoms, each of which is optionally substituted by halogen, hydroxyl or carboxyl, by straight-chain or branched alkoxycarbonyl having up to 6 carbon atoms or by a group of the formula —$NR^2R^3$, in which $R^2$ and $R^3$ are identical or different and denote hydrogen, straight-chain or branched alkyl having up to 8 carbon atoms or phenyl, or $R^2$ and $R^3$, together with the nitrogen atom, form a 5- to 7-membered, saturated or unsaturated heterocyclic ring having up to 2 further heteroatoms from the series comprising S, N and O, or alkyl or alkenyl are optionally substituted by phenyl which in turn can-be substituted up to 5 times by identical or different halogen and their physiologically acceptable salts.

Physiologically acceptable salts of the 6-thionodibenz[b,e]azepines can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Heterocycle in general represents a 5- to 7-membered, preferably 5- to 6-membered, saturated or unsaturated ring which as hetero atoms can contain up to 2 oxygen, sulphur and/or nitrogen atoms. Preferred 5- and 6-membered rings are those having an oxygen, sulphur and/or up to 2 nitrogen atoms. The following are mentioned as particularly preferred: pyrrolyl, pyrazolyl, pyridyl, pyrimidyl, pyrazinyl, pyridazinyl, thiazolyl, oxazolyl, imidazolyl, isoxazolyl, pyrrolidinyl, piperidinyl, piperazinyl, tetrazolyl or morpholinyl.

The compounds according to the invention can exist in stereoisomeric forms, which either behave as image and mirror image (enantiomers), or which do not behave as image and mirror image (diastereomers). The invention relates both to the antipodes and to the racemic forms as well as to the diastereomer mixtures. The racemic forms can be separated, like the diastereomers, into the stereoisomerically uniform constituents in a known manner [cf. E. L. Eliel, Stereochemistry of Carbon Compounds, McGraw Hill, 1962].

In the radical of the general formula (II)

the C=N double bond can have either the E- or the Z-configuration, or E/Z mixtures can be present.

Preferred compounds of the general formula (I) are those in which

A, B and D are identical or different and represent hydrogen, fluorine, chlorine, hydroxyl, trifluoromethyl, trifluoromethoxy or straight-chain or branched alkyl or alkoxy each having up to 6 carbon atoms, E represents hydrogen or straight-chain or branched alkyl having up to 4 carbon atoms, $R^1$ represents hydrogen or represents cyclopropyl, cyclopentyl, cyclohexyl or 2-tetrahydropyranyl, or represents straight-chain or branched acyl having up to 6 carbon atoms, or represents straight-chain or branched alkyl or alkenyl each having up to 8 carbon atoms, each of which can optionally be substituted by fluorine, hydroxyl or carboxyl, by straight-chain or branched alkoxycarbonyl having up to 4 carbon atoms or by a group of the formula —$NR^2R^3$, in which $R^2$ and $R^3$ are identical or different and denote hydrogen or straight-chain or branched alkyl having up to 6 carbon atoms, or $R^2$ and $R^3$, together with the nitrogen atom, form a morpholine or piperazine ring, or alkyl is optionally substituted by phenyl which in turn can be substituted up to 5 times by identical or different fluorine, chlorine or bromine and their physiologically acceptable salts.

Particularly preferred compounds of the general formula (I) are those
in which

A, B and D are identical or different and represent hydrogen, fluorine, chlorine or straight-chain or branched alkyl or alkoxy each having up to 4 carbon atoms, E represents hydrogen, methyl or ethyl, $R^1$ represents hydrogen or represents cyclopropyl or 2-tetrahydropyranyl, or represents straight-chain or branched acyl having up to 4 carbon atoms, or represents straight-chain or branched alkyl or alkenyl each having up to 6 carbon atoms, each of which is optionally substituted by hydroxyl, carboxyl, fluorine, methoxycarbonyl, ethoxycarbonyl or propoxycarbonyl or by a group of the formula —$NR^2R^3$, in which $R^2$ and $R^3$ are identical or different and denote hydrogen or straight-chain or branched alkyl having up to 4 carbon atoms, or R² and R³ together with the nitrogen atom, form a morpholine ring, or alkyl is optionally substituted by phenyl which in turn can be substituted up to 5 times by identical or different fluorine or chlorine and their physiologically acceptable salts.

In addition, a process for the preparation of the compounds of the general formula (I) according to the invention has been found, characterised in that compounds of the general formula (III)

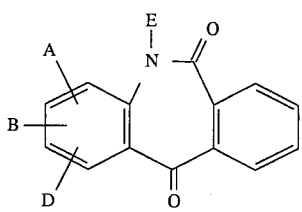

in which

A, B, D and E have the abovementioned meaning, are first reacted with hydroxylamines of the general formula (IV)

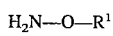

in which

R¹ has the abovementioned meaning, in inert solvents, if appropriate in the presence of a base and then the carbonyl function adjacent to the —N—E group is converted into a thiocarbonyl function using Lawesson's reagent, and, if appropriate, the substituents A, B, D and R¹ are varied according to customary chemical methods, and in the case in which E does not denote hydrogen, an alkylation is likewise carried out according to known methods.

The process according to the invention can be illustrated by way of example by the following reaction scheme:

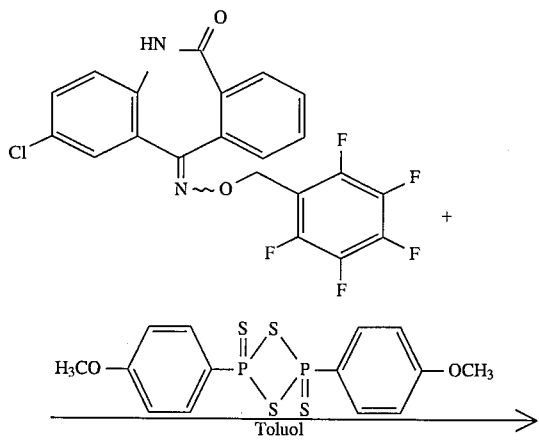

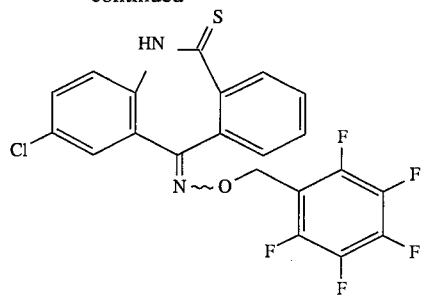

Suitable solvents for the two process steps are the customary organic solvents which do not change under the reaction conditions. These preferably include ethers such as diethyl ether, dioxane, tetrahydrofuran, glycol dimethyl ether, or hydrocarbons such as benzene, toluene, xylene, hexane, cyclohexane or mineral oil fractions, or halogenohydrocarbons such as dichloromethane, trichloromethane, tetrachloromethane, dichloroethylene, trichloroethylene or chlorobenzene, or ethyl acetate, or triethylamine, pyridine, dimethyl sulphoxide, dimethylformamide, hexamethylphosphoric triamide, acetonitrile, acetone or nitromethane. It is also possible to use mixtures of the solvents mentioned. Pyridine is preferred for the 1st reaction step and toluene for the second.

Suitable bases are the customary basic compounds. These preferably include alkali metal or alkaline earth metal carbonates such as sodium carbonate or potassium carbonate, or alkali metal alkoxides such as, for example, sodium methoxide or ethoxide, potassium methoxide or ethoxide or potassium tert-butoxide, or organic amines such as benzyltrimethylammoniumhydroxide, tetrabutylammonium hydroxide, pyridine, triethylamine or N-methylpiperidine.

The process steps are in general carried out in a temperature range from +30° C. to +150° C., preferably from +50° C. to +120° C.

The process is in general carried out at normal pressure. However, it is also possible to carry out the process at reduced pressure or at elevated pressure (for example in a range from 0.5 to 5 bar).

Suitable solvents for the alkylation (E≠H) are likewise customary organic solvents which do not change under the reaction conditions. These preferably include ethers such as diethyl ether, dioxane, tetrahydrofuran, glycol dimethyl ether, or hydrocarbons such as benzene, toluene, xylene, hexane, cyclohexane or mineral oil fractions, or halogenohydrocarbons such as dichloromethane, trichloromethane, tetrachloromethane, dichloroethylene, trichloroethylene or chlorobenzene, or ethyl acetate, or triethylamine, pyridine, dimethyl sulphoxide, dimethylformamide, hexamethylphosphoric triamide, acetonitrile, acetone or nitromethane. It is also possible to use mixtures of the solvents mentioned. Acetone is preferred.

The alkylation is carried out in the abovementioned solvents at temperatures of 0° C. to +150° C., preferably at room temperatures up to +100° C., at normal pressure.

The compounds of the general formula (III) are known per se or can be prepared according to customary methods [cf., for example, U.S. Pat. No. 3,431,257].

The hydroxylamines of the general formula (IV) are also known or can be prepared according to methods known from the literature.

The inhibitors described herein are inhibitors of reverse transcriptase and can be employed as such for all purposes for which enzyme inhibitors are suitable. This is, for example, use in diagnosis in order to improve the precision and selectivity of enzyme activity measurements. In affinity chromatography, they can be used as an affinity label and in research they can be used for the elucidation of reaction mechanisms of enzymatic reactions.

Moreover, it has surprisingly been found that the compounds of the general formula (I) according to the invention have an extremely strong action against retroviruses. They show activity in lentivirus-infected cell cultures. It was possible to show this by way of the HIV virus.

HIV Infection in Cell Culture

The HIV test was carried out with slight modifications according to the method of Pauwels et al. [cf. Journal of Virological Methods 20, (1988), 309–321].

Normal human blood lymphocytes (PBLs) were concentrated by means of Ficoll-Hypaque and stimulated with phytohaemagglutinin (90 µg/ml) and interleukin-2 (40 U/ml) in RPMI 1640 and 20% foetal calf serum. For infection with the infectious HIV, PBLs were pelleted and the cell pellet was then suspended in 1 ml of HIV virus adsorption solution and incubated for 1 hour at 37° C.

Alternatively, HIV-susceptible H9 cells were employed instead of normal human blood lymphocytes for testing the antiviral effects of the compounds according to the invention.

The virus adsorption solution was centrifuged and the infected cell pellet was taken up in growth medium so that a concentration of $1 \times 10^5$ cells per ml was established. The cells infected in this way were pipetted into the wells of 96-well microtiter plates to give $1 \times 10^4$ cells/well.

The first vertical row of the microtiter plate contained only growth medium and cells which had not been infected, but otherwise treated exactly as described above (cell control). The second vertical row of the microtiter plate contained only HIV-infected cells (virus control) in growth medium. The other wells contained the compounds according to the invention in differing concentrations, starting from the wells of the 3rd vertical row of the microtiter plate, from which the test substances were diluted $2^{10}$ times in 2-fold steps.

The test batches were incubated at 37° C. until, in the untreated virus control, the syncytia formation typical of HIV occurred (between day 3 and 6 after infection), which was then microscopically assessed. Under these test conditions, in the untreated virus control about 20–50 syncytia resulted, while the untreated cell control contained no syncytia.

The $IC_{50}$ values were determined as the concentration of the treated and infected cells at which 50% (about 10–20 syncytia) of the virus-induced syncytia were suppressed by treatment with the compound according to the invention.

It has now been found that the compounds according to the invention protect HIV-infected cells from virus-induced cell destruction.

TABLE 1

| Ex. No. | $IC_{50}$ (µM) |
|---|---|
| 2 | 1.5 |
| 3 | 0.38 |
| 4 | 0.38 |
| (comparison) | |
| BIRG 587 | 0.09 |

TABLE 1-continued

| Ex. No. | $IC_{50}$ (µM) |
|---|---|
| [J.Med. Chem. 34 2231, (1991)] | |

The compounds according to the invention are useful active substances in human and veterinary medicine for the treatment and prophylaxis of diseases caused by retroviruses.

Indication areas in human medicine which can be mentioned are, for example:

1.) The treatment and prophylaxis of human retrovirus infections.

2.) For the treatment or prophylaxis of diseases (AIDS) caused by HIV I (human immunodeficiency virus; formally called HTLV III/LAV) and HIV II and the stages associated therewith such as ARC (AIDS-related complex) and LAS (lymphadenopathy syndrome) and also the immunodeficiency and encephalopathy caused by this virus.

3.) For the treatment or the prophylaxis of an HTLV-I or HTLV-II infection.

4.) For the treatment or the prophylaxis of the AIDS-carrier state (AIDS-transmitter state).

Indications in veterinary medicine which can be mentioned are, for example:

Infections with a) Maedivisna (in sheep and goats)

b) progressive pneumonia virus (PPV) (in sheep and goats)

c) caprine arthritis encephalitis virus (in sheep and goats)

d) Zwoegerziekte virus (in sheep)

e) infectious anaemia virus (of the horse)

f) infections caused by feline leukaemia virus g) infections caused by feline immunodeficiency virus (FIV)

h) infections caused by simian immunodeficiency virus (SIV)

The abovementioned items 2, 3 and 4 are preferred from the indication area in human medicine.

The present invention includes pharmaceutical preparations which, in addition to non-toxic, inert pharmaceutically suitable excipients, contain one or more compounds of the formula (I) or which consist of one or more active substances of the formula (I), and processes for the production of these preparations.

The active substances of the formula (I) should preferably be present in the abovementioned pharmaceutical preparations in a concentration of about 0.1 to 99.5% by weight, preferably of about 0.5 to 95% by weight, of the total mixture.

Apart from the compounds of the formula (I), the abovementioned pharmaceutical preparations can also contain other pharmaceutical active substances.

The abovementioned pharmaceutical preparations are produced in a customary manner by known methods, for example by mixing the active substance or substances with the excipient or excipients.

In general, it has proved advantageous both in human and in veterinary medicine to administer the active substance or substances according to the invention in total amounts of about 0.1 to about 200 mg/kg, preferably 1 to 100 mg/kg of body weight every 24 hours, if appropriate in the form of several individual doses, to achieve the desired results. An individual dose contains the active substance or substances preferably in amounts of about 1 to about 80, in particular 1 to 30, mg/kg of body weight. However, it may be necessary to depart from the dosages mentioned, in particular depending on the nature and the body weight of the subject to be treated, the type and the severity of the disease, the type of preparation and the administration of the medicament as well as the time or interval within which administration takes place.

PREPARATION EXAMPLES

Example 1

(E/Z)-2-Chloro-11-(pentafluorophenyl)methoxyimino-6-thiono- 5,6-dihydro-11H-dibenz[b,e]azepine

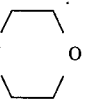

200 mg (0.44 mmol) of 2-chloro-11-(pentafluorophenyl)-methoxyimino- 6-oxo-5,6-dihydro-11H-dibenz[b,e]azepine in 3.5 ml of toluene are treated with 89 mg (0.22 mmol) of Lawesson's reagent and heated under reflux for 3 h. The mixture is then concentrated and the residue is purified on silica gel using toluene/petroleum ether 20:1.

Yield: 163 mg $^1$H-NMR (CDCl$_3$)+DMSO): δ=5.30 (s, 2H); 7.20–7.50 (m, 6H); 8.27 (d,J=8 Hz, 1H); 12.47 (s,NH).

The examples shown in Table 1 are prepared in analogy to the procedure of Example 1:

TABLE 1

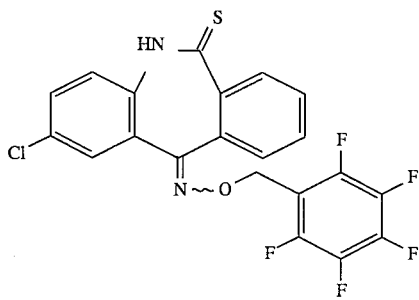

| Ex. No. | A | E | R$^1$ | E/Z |
|---|---|---|---|---|
| 2 | Cl | H | —(CH$_2$)$_2$N(CH$_3$)$_2$ | 1:1 |
| 3 | Cl | H | —(CH$_2$)$_2$—N⟨O⟩ | 1:1 |
| 4 | Cl | H | —CH$_3$ | 1:1 |
| 5 | Cl | —CH$_3$ | —CH$_3$ | 1:1 |
| 6 | Cl | H | —C$_2$H$_5$ | 1:1 |
| 7 | Cl | H | —C(CH$_3$)$_3$ | 1:1 |
| 8 | Cl | H | —CH$_2$—CH=CH$_2$ | 1:1 |

TABLE 1-continued

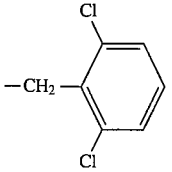

| Ex. No. | A | E | R$^1$ | E/Z |
|---|---|---|---|---|
| 9 | Cl | H | —CH$_2$—(2,6-Cl$_2$C$_6$H$_3$) | 1:1 |
| 10 | Cl | H | —CH$_2$—CO$_2$CH$_3$ | 1:1 |
| 11 | Cl | —CH$_3$ | —CH$_2$—CO$_2$CH$_3$ | 1:1 |
| 12 | Cl | H | —CH$_2$—CO$_2$—C$_2$H$_5$ | 1:1 |
| 13 | Cl | —CH$_3$ | —CH$_2$CO$_2$C$_2$H$_5$ | 1:1 |
| 14 | Cl | H | —(CH$_2$)$_4$CO$_2$C$_2$H$_5$ | 1:1 |
| 15 | Cl | H | —CO—CH$_3$ | 1:1 |

We claim:
1. 6-Thiono-dibenz[b,e]azepines of the formula (I):

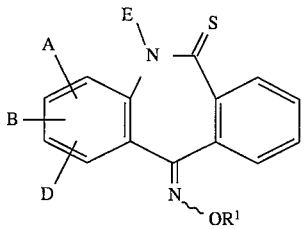

in which
A, B and D are identical or different and represent hydrogen, amino, nitro, halogen, cyano, hydroxyl, trifluoromethyl, trifluoromethoxy or straight-chain or branched alkyl or alkoxy each having up to 8 carbon atoms;

E represents hydrogen or straight-chain or branched alkyl having up to 6 carbon atoms;

R$^1$ represents cycloalkyl having 3 to 6 carbon atoms, or represents 2-tetrahydropyranyl, or represents straight-chain or branched carboxylic acid acyl having up to 8 carbon atoms, or represents C$_{2-10}$-alkenyl, or represents straight-chain or branched alkyl or alkenyl each having up to 10 carbon atoms, each of which is substituted by halogen, hydroxyl, carboxyl, or straight-chain or branched alkoxycarbonyl having up to 6 carbon atoms, or alkyl or alkenyl are substituted by phenyl which in turn can be substituted up to 5 times by identical or different halogen,
and their physiologically acceptable salts.

2. Compounds of the formula (I) according to claim 1, in which

A, B and D are identical or different and represent hydrogen, fluorine, chlorine, hydroxyl, trifluoromethyl, trifluoromethoxy or straight-chain or branched alkyl or alkoxy each having up to 6 carbon atoms, E represents hydrogen or straight-chain or branched alkyl having up to 4 carbon atoms, $R^1$ represents cyclopropyl, cyclopentyl, cyclohexyl or 2-tetrahydropyranyl, or represents straight-chain or branched carboxylic acid acyl having up to 6 carbon atoms, or represents $C_{2-8}$-alkanyl, or represents straight-chain or branched alkyl or alkenyl each having up to 8 carbon atoms, each of which is substituted by fluorine, hydroxyl or carboxyl, or by straight-chain or branched alkoxycarbonyl having up to 4 carbon atoms, or alkyl is substituted by phenyl which in turn can be substituted up to 5 times by identical or different fluorine, chlorine or bromine and their physiologically acceptable salts.

3. Compounds of the formula (I) according to claim 1, in which

A, B and D are identical or different and represent hydrogen, fluorine, chlorine or straight-chain or branched alkyl or alkoxy each having up to 4 carbon atoms, E represents hydrogen, methyl or ethyl, $R^1$ represents cyclopropyl or 2-tetrahydropyranyl, or represents straight-chain or branched carboxylic acid acyl having up to 4 carbon atoms, or represents $C_{2-6}$-alkenyl, or represents straight-chain or branched alkyl or alkenyl each having up to 6 carbon atoms, each of which is substituted by hydroxyl, carboxyl, fluorine, methoxycarbonyl, ethoxycarbonyl or propoxycarbonyl, of the formula —$NR^2R^3$, or alkyl is substituted by phenyl which in turn can be substituted up to 5 times by identical or different fluorine or chlorine and their physiologically acceptable salts.

* * * * *

UNITED STATES PATENT AND TRADEMARK OFFICE
CERTIFICATE OF CORRECTION

PATENT NO. : 5,545,736
DATED : August 13, 1996
INVENTOR(S) : Wild, et al.

It is certified that error appears in the above-indentified patent and that said Letters Patent is hereby corrected as shown below:

Title Page, item:[45]: After Date of Patent: insert -- * --

Col. 10, line 11  Delete " of the formula $-NR^2R^3$ "

Signed and Sealed this

Thirty-first Day of December, 1996

Attest:

BRUCE LEHMAN

Attesting Officer        Commissioner of Patents and Trademarks